United States Patent [19]

Hedberg et al.

[11] Patent Number: 5,623,941
[45] Date of Patent: Apr. 29, 1997

[54] CERVICAL SAMPLING VELOUR BRUSH

[75] Inventors: Tommy Hedberg; Jan Claren, both of Lund, Sweden

[73] Assignee: Nils Stormby, Malmo, Sweden

[21] Appl. No.: 443,822

[22] Filed: May 18, 1995

Related U.S. Application Data

[63] Continuation of Ser. No. 265, Jan. 4, 1993, abandoned, which is a continuation-in-part of Ser. No. 674,127, Oct. 3, 1991, abandoned.

[30] Foreign Application Priority Data

May 10, 1988 [SE] Sweden ................................ 8801764-5

[51] Int. Cl.$^6$ ................................................ A61B 10/00
[52] U.S. Cl. ................................................ 128/756; 128/759
[58] Field of Search ................................ 128/756, 757, 128/759, 749, 750; 15/104.001, 159.1, 160, 176.1, 179, 185, 210.1, 221

[56] References Cited

U.S. PATENT DOCUMENTS

| | | |
|---|---|---|
| 27,010 | 5/1860 | Mason . |
| D. 122,019 | 8/1940 | Hahn . |
| D. 247,936 | 5/1978 | Wortley, Jr. et al. . |
| 1,323,604 | 12/1919 | Marinelli . |
| 2,767,703 | 10/1956 | Nieburge . |
| 2,955,591 | 10/1960 | MacLean . |
| 3,592,186 | 7/1971 | Oster . |
| 3,881,464 | 5/1975 | Levene . |
| 4,059,404 | 11/1977 | Schuster et al. ............. 128/760 |
| 4,164,046 | 8/1979 | Cooley . |
| 4,227,537 | 10/1980 | Suciu et al. . |
| 4,485,515 | 12/1984 | Hagedorn et al. . |
| 4,486,915 | 12/1984 | Stewart et al. ................. 15/187 |
| 4,494,268 | 1/1985 | Chu ................................ 15/176 |
| 4,517,687 | 5/1985 | Liebig et al. . |
| 4,527,575 | 7/1985 | Vasas ............................ 132/218 |
| 4,754,764 | 7/1988 | Bayne . |
| 4,767,619 | 8/1988 | Murray . |
| 4,850,073 | 7/1989 | Preuss . |
| 4,958,402 | 9/1990 | Weihraueh ................... 15/207.2 |
| 4,978,504 | 12/1990 | Nason . |
| 5,191,899 | 3/1993 | Strickland et al. ............ 128/756 |
| 5,201,323 | 4/1993 | Vermeulen ................... 128/756 |

FOREIGN PATENT DOCUMENTS

| | | |
|---|---|---|
| 239270 | 9/1987 | European Pat. Off. . |
| 292693 | 11/1988 | European Pat. Off. . |
| 420047 | 9/1976 | Sweden . |
| 421993 | 1/1982 | Sweden . |
| 812038 | 3/1982 | Sweden . |
| 1553438 | 9/1979 | United Kingdom . |
| 1573819 | 8/1980 | United Kingdom . |
| 9116855 | 11/1991 | WIPO ............................. 128/756 |

OTHER PUBLICATIONS

Cervical Cancer Test Pamphlet by Medscand. Date unknown, Author unknown.
Belknap Hardward & Manufacturing Co., ©1940, Furnace Brush, item No. H718 (Copy in Group 290). (Author unknown).
John Pritzlaff Hardware Co., 1937, Furnace Brush, top left of p. 139 (Copy in Group 290). (Author unknown).
Morley–Murphy Co., 1942, Brush item No. 560, p. 952 (Copy in Group 290). (Author unknown).

(List continued on next page.)

*Primary Examiner*—Stephen C. Pellegrino
*Assistant Examiner*—Guy V. Tucker
*Attorney, Agent, or Firm*—Merchant, Gould, Smith, Edell, Welter & Schmidt, P.A.

[57] ABSTRACT

The invention relates to a brush comprising a shank which over a portion of the length thereof is provided wish a velour finish of fibers which are attached to the shank and stand on end projecting from the surface of the shank. The invention also relates to a method in manufacturing such a brush wherein an end portion of the shank is dipped in glue and fibers then are applied to said portion by being adhered to the shank by means of an electrostatic field so as to be attached to the end portion coated with glue.

14 Claims, 5 Drawing Sheets

OTHER PUBLICATIONS

Sklar Products, 1982, Cleaning Brush, botton left of page 73; Cleaning Brush item 78–2821 thru 78–2833 (Copy in Group 290). (Author unknown).

Sklar Products, 1982, Cleaning Brush, page number unknown, Cleaning Brush item 78–2812, 78–2821 thru 78–2823. (Author unknown).

Catalog page from the catalog "Manufrance", 1973, page unknown (Author unknown).

CERVICAL SAMPLING VELOUR BRUSH

This is a File Wrapper Continuation of application Ser. No. 08/000265, filed 4 Jan. 1995, now abandoned which is a contruction in-part of Ser. No. 07/634,127, filed Jan. 3, 1991, now abandoned.

BACKGROUND OF THE INVENTION

The invention relates to a brush, particularly for medical use, for collecting material and for retaining such material for transfer of the material from a collection cite to a deposit site where the collected material is deposited by smearing on a surface, and a method in manufacturing such a brush.

For medical sampling in body cavities and body passages there are used in addition to spatulas and cotton swabs, such swabs consisting of a shank with a cotton wad at one end thereof, also brushes because these, contrary to spatulas and cotton swabs, can be made of a material and with a stiffness and density which are adapted to the surface of the body at which the sampling is to be effected, in order to scrape sufficiently effectively on said surface as is required in order that cells or surface fragments and/or secrete sought for shall be collected in and or shall adhere to the brush, and the brush at the same time can be constructed in such a way that it is possible to perform a gentle and, as far as possible, painless sampling. A further advantage of the sampling brush is that the collected sample can be easily transferred from the brush by smearing on a microscope slide or by washing in a liquid without the collected cells being damaged or destroyed. Sampling brushes are used at present for sampling e.g. in uterus, cervix or urethra.

In present embodiments sampling brushes comprise a shank of twisted wire and bristles or tufts are attached to the shank by being clamped between the twisted wires. Such sampling brushes are shown and described e.g. in U.S. Pat. No. 4,227,537 (Suciu et al) and U.S. Pat. No. 3,881,464 (Levene). A major drawback of brushes of this type is that it is necessary to cut the bristles after the attachement thereof to impart to the brush the desired diameter. Also, the bristles are not distributed uniformly around the twisted wires. They are concentrated to a number of sectors mutually spaced by sectors free of bristles, the number of sectors being dependent of the number of twisted wires forming the shank, if two wires are used as is common practice, there will be four bristle sectors. The bristles are randomly distributed in the sectors, and the angle enclosed by adjacent bristles cannot be controlled. This reduces effectiveness of the brush in collecting material. There is an optimal number of bristles that can be attached to the shank between the wires. If the number of bristles is larger than said optimal number there is the risk of bristles loosening from the shank, which maybe hazardeous e.g. when the brush is used for medical sampling in body cavities. Moreover, the manufacture of such brushes is expensive and no doubt is too expensive for a one-way product as is concerned here, and the possibilities to make small brushes, i.e. brushes wherein the brush portion has a small diameter, and to make brushes with very thin bristles, i.e. softer brushes, are very limited. However, it is desired to provide small and soft brushes and also to reduce the manufacturing costs of the brushes.

SUMMARY OF THE INVENTION

The purpose of the invention is to attain this particularly in case of brushes for medical sampling of the kind referred to above, e.g. for sampling in urethra, but the invention as to the broadest aspect thereof is not limited to brushes for sampling purposes because the invention is of importance also to brushes for other medical uses such as application of therapeutic substances or refrigerants on and in the human body, and also to brushes outside the medical field, e.g. brushes for application of cosmetics, particularly mascara, because brushes for this purpose should be kind to the sensitive skin on the eyelid and at the same time should be able to penetrate between the hairs of the eyelash.

For the purpose mentioned above the invention provides a brush for collecting material and for retaining such material for transfer of the material from a collection site to a deposit site where the collected material is deposited by smearing on a surface, comprising a shank; a body projecting axially from one end of the shank, the body having a generally circular cross section; and a velour finish covering the body, the velour finish including fibers which are attached to the body and stand on end projecting from the surface of the body. For the manufacture of such a brush the invention also provides a method in manufacturing a brush comprising a shank having an end portion, which comprises a velour finish including fibers, wherein said end portion of the shank is dipped in glue; and said fibers are then applied to the end portion by means of an electrostatic field so as to be attached to said end portion standing on end projecting from the surface of the end portion.

The velour finishing technique per se is previously known in order to impart to surfaces the character of being covered with velvet but is applied here for a completely new purpose, viz. to provide a rough brushlike surface on a body.

U.S. Pat. No. 4,850,073 (Preuss) discloses a fiber pile brush for cleaning textile fabrics, comprising a support head provided with a synthetic fiber pile covering. Such covering may comprise a nylon velour of unidirectional fibers and forms two areas one on each side of a collection zone, the pile covering in said areas having opposing orientation, which means that the fibers form an angle with the direction perpendicular to the support head.

BRIEF DESCRIPTION OF THE DRAWINGS

Illustrative embodiments of the invention are shown in the accompanying drawings wherein.

DETAILED DESCRIPTION OF THE PREFERRED EMBODIMENT

Figure 1:
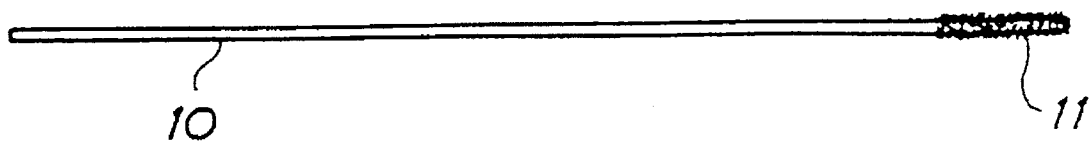
FIG. 1 is a side view of a sampling brush having cylindrical shape.

Referring to FIG. 1 of the drawings a brush for medical use, in this case for medical sampling in the mouth of cervix, comprises a shank 10 which can consist of a solid or tubular plastics rod which is rigid or of such character that it can be bent plastically or elastically. One end portion of the shank is provided with fibers 11 applied by velour finishing said portion.

Figure 2:
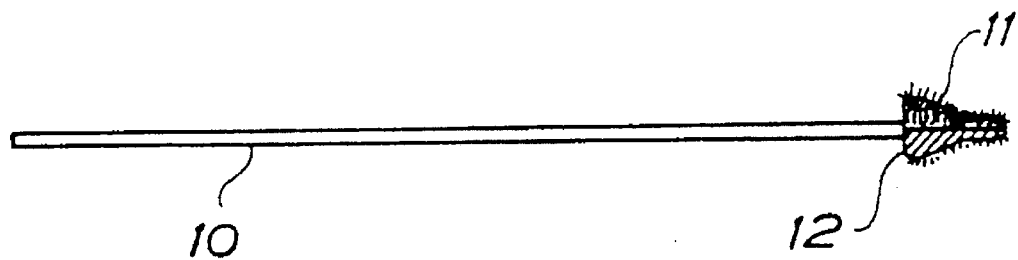
FIG. 2 is a half side view of end a half axial cross-sectional view of a sampling brush having a particular shape adapted to the sampling place.

It is not necessary that the brush is made substantially cylindrical as in FIG. 1. The brush may also be given another shape, e.g. conical shape or a shape which is adapted to the shape of the sampling place. An embodiment of the last-mentioned type is shown in FIG. 2. A body 12 is shaped so as to conform substantially with the shape of the sampling place and is attached to or is integral with the shank 10, and the surface of this body then has been velour finished.

The fibers forming the brush are of uniform length and project perpendicularly from the surface to which they are attached perpendicularly to the tangent thereof. Accordingly, the shape of said surface defines the shape of the brush.

In a specific embodiment of the brush in FIG. 1 intended for sampling in urethra, the shank is resilient and preferably is made very thin and is tapering from the handle end towards the brush end in order that the shank very easily shell adjust itself to urethra when it is inserted thereinto. Such a brush can have e.g. a minimum diameter of the shank at the brush end, which is 0.8 mm, and a maximum diameter at the handle end, which is 1.5 mm, the brush proper (the velour finish pot%ion) having a length of 0.5 mm. A brush constructed in this way has been found to cause considerably less pain when sampling in urethra than conventional brushes having a shank of wire and bristles attached thereto.

By applying the velour finishing technique there are provided unlimited possibilities of adjusting the brush to the specific sampling for which the brush is intended.

Figure 3:
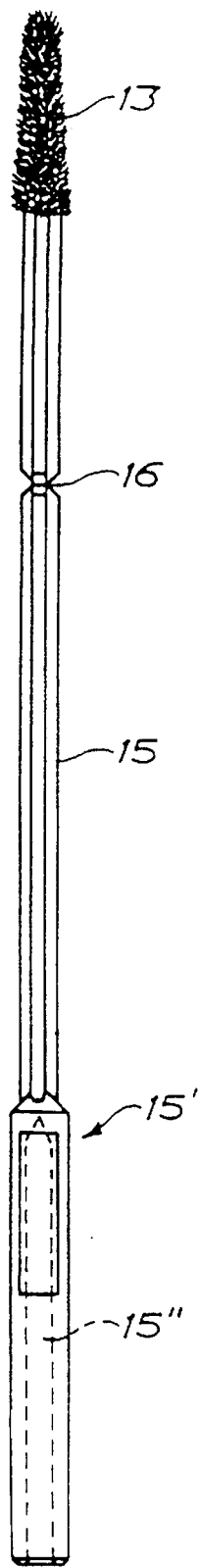
FIG. 3 is a side view of a brush of the invention having conical shape.

The brush in FIG. 3 comprises a conical body 13 which is integral with a shank 15 and forms a central pin portion of one end of the shank. Preferably the shank has cross-shaped cross-section so as to have sufficient rigidity, said shank forming a handle 15' of cylindrical shape at the other end thereof. Preferably, the shank is produced by injection molding of a suitable plastics material, e.g. polypropylene. For technical reasons from the manufacturing point of view an axial bottom hole 15" is provided in the handle to avoid concentration of material in the handle, which could cause impressions the outside surface of the handle and disturb the cylindrical shape thereof. The conical body has velour finish at the conical surface thereof. The fibers of a brush for cytological sampling in the embodiment shown in FIG. 3, typically can have a length of the order of 2 mm and a diameter of the order of 0.12 mm. Such a brush has been found to cause less tendency of bleeding at sampling than such conventional brushes which are made with a shank of twisted wire having bristles attached thereto. A break-point 16 is arranged spaced from the conical body so that the end portion of the brush can be broken off when it is inserted into a test tube used for treating or transporting the sample that has been taken. Two or more break-points may be provided.

Figure 4:
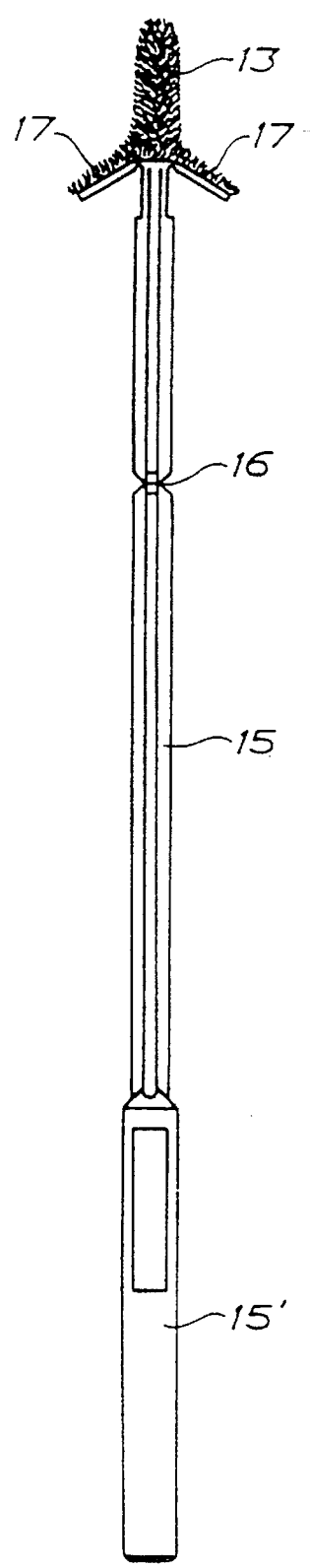
FIGS. 4 and 5 are two side views perpendicular to each other of a further development of the brush of FIG. 3 having a shape which is adapted to the sampling place.
Figure 5:
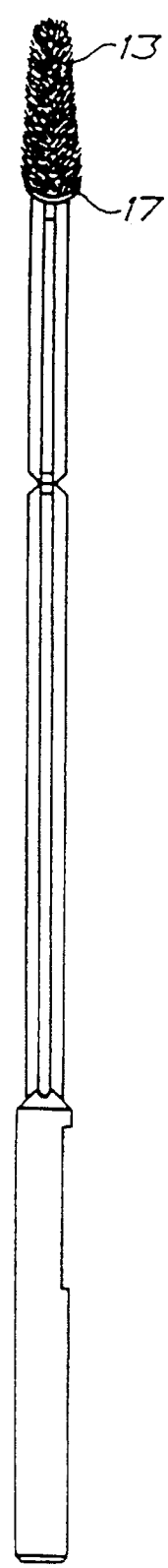

The further development of the brush of FIG. 3 which is shown in FIGS. 4 and 5 comprises two flaps 17 on the conical portion 13, said flaps being connected to said portion by means of integral hinges and are slightly curved so that they can be bent towards the shank and partly enclose the shank, e.g. when the brush after sampling is rolled against a microscope slide for smearing the sample thereon. The brush is shaped particularly for sampling in the cervical mouth.

In the embodiment of FIG. 4 and 5 the flaps 17 may be rigidly connected to the shaft or form an integral part thereof, the conical portion 13 forming a central pin portion projecting coaxially from the shank 15 between the flaps 17.

Figure 6:
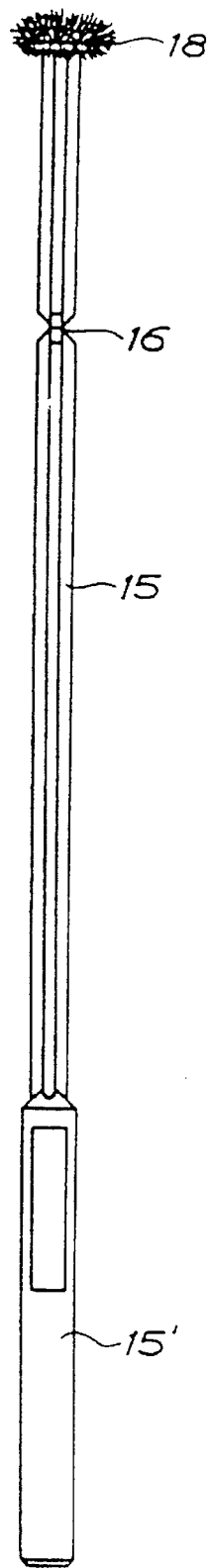
FIG. 6 is a side view of a sampling brush having velour finish provided on a circular disk.

The brush in FIG. 6 has a circular disk 18 velour finish, to which the shank is attached centrally and axially. This brush can be used for sampling but it is also very useful for applying medicaments at therapeutic treatment of local portions, such as warts, on the human body, or for applying a refrigerant (nitrogen) at cryotherapy.

Figure 7:
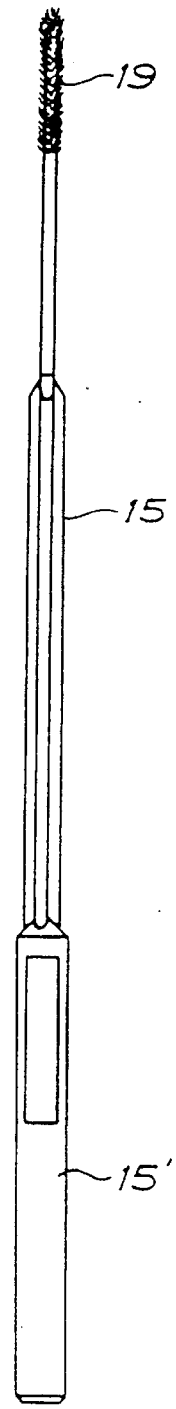
FIG. 7 is a side view of a uretra brush.

The brush in FIG. 7 has a velour finish portion 19 which has a substantially smaller cross dimension than the shank, and this brush is intended for use as a urethra brush.

Figure 8:
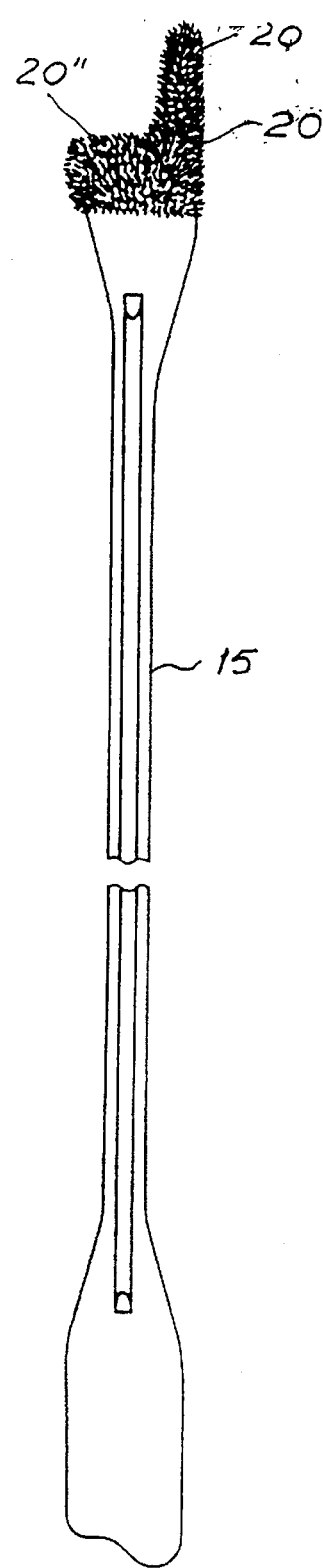
FIG. 8 is a side view of a brush provided on a conventional spatula.

As shown in FIG. 8 a conventional spatula for sampling in the cervical mouth is provided with a velour finish region 20. This region forms a portion 20' projecting An the longitudinal direction of the shank 15 beyond a side portion 20" at one side of portion 20'. However, in a modified embodiment portion 20' may be located centrally between two side potions forming two wings one at each side of the central portion 20'.

Figure 9:
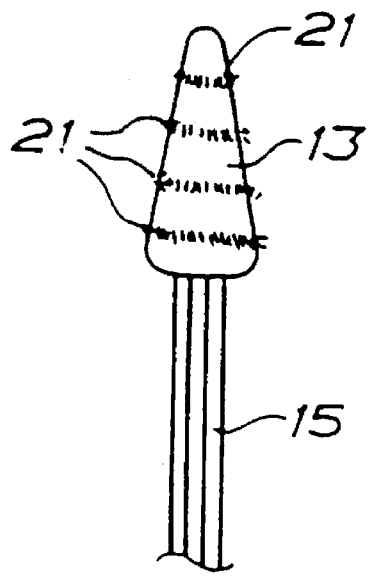
FIG. 9 is a side view of a conical brush having annular portions with velour finish.
Figure 10:
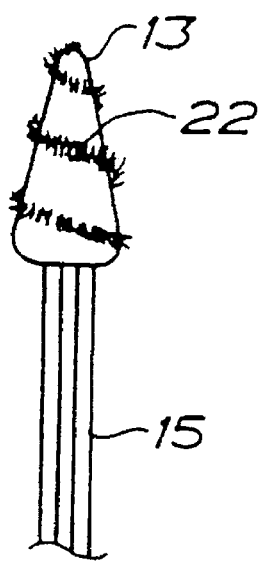
FIG. 10 is a view of a helically extending velour finish.
Figure 11:
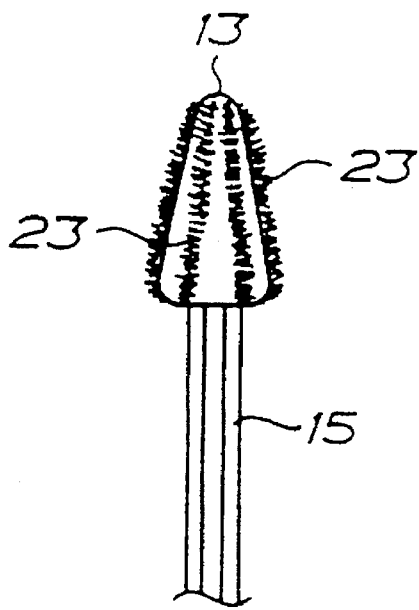
FIG. 11 is a side view of a conical brush having axial portions with velour finish.

The velour finish surface can be divided into a number of axially mutually spaced annular velour finish portions 21 according to FIG. 9, or can form a helically extending string 22, as shown in FIG. 10. The velour finish surface can also include a number of peripherally mutually spaced axial portions 23 according to FIG. 11.

The brush of the invention is kind to the tissues and at the same time is effective as far as scraping of secrete, surface fragments or cells is concerned. Moreover, the brush has a pronounced ability of retaining such material as has been collected by the sampling or such material as has been taken up by means of the brush so as to be applied to the human body, the brush at the same time willingly giving off such material when smeared on a microscope slide or the skin, respectively. The brush also has the ability to penetrate between the hairs of the eyelash when used for applying mascara, and it is not easily clogged when it is used for such application; the brush will stand fluffy also after having been used for a long time.

The method of the invention for manufacturing the brushes described will be explained in more detail with reference to FIGS. 12 to 16.

The shanks 15 for several brushes can be injection molded in a single shot and in that case are integrally connected at an ingot 24 as shown in 12, wherein the brush shanks are assumed to be of the embodiment of FIG. 7. The ingot is plate-shaped and is relatevely thin, and between adjacent shanks the ingot is made thinner to form transverse hinges 25 which facilitate bending of the ingot in the plane thereof. For the manufacture of the brushes the shanks are to be advanced along a process line along which there are provided several working stations, and this transport takes place with the shanks integral with each other in the manner shown in FIG. 12. A metal profile 26 of the kind shown in FIG. 13 can be used for guiding the integral shanks along the line. This profile has a groove 27 dimensioned to receive therein the ingot 24 and to support same, and it has also at the sides thereof underout grooves for mounting the profile in a frame or the like.

For advancement of the shanks there can be provided in the profile 26 apertures at the sides thereof for engagement of driven clamp rollers with the sides of the ingot, or another drive means can be provided, such means being easily proposed by the skilled man.

Figure 12:
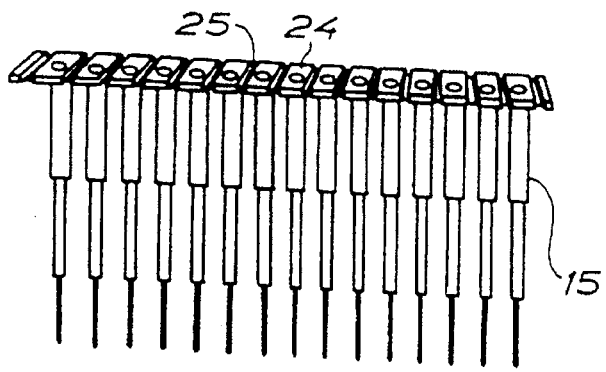
FIG. 12 is a perspective view of a number of brush shanks which have been produced by injection molding and are integral via a plate-shaped ingot.
Figure 13:
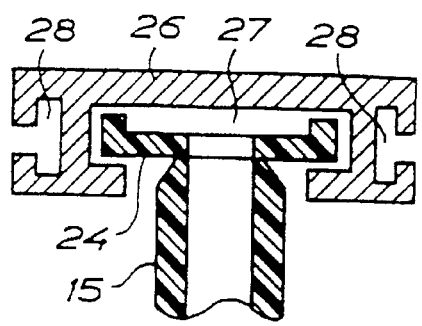
FIG. 13 is a cross-sectional view of a guide rail for guiding the molding of FIG 1 in a process line.
Figure 14:
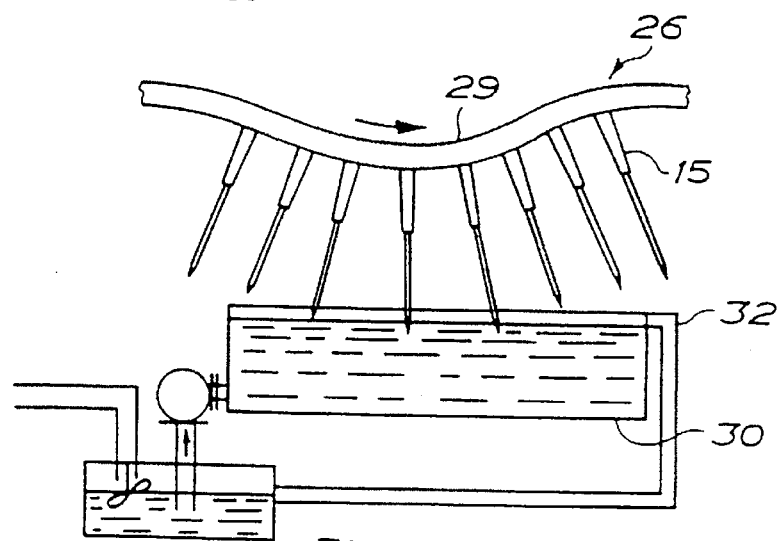
FIG. 14 is a diagrammatic side view of apparatus for applying glue to the shank ends in a station along the process line.

When the shanks of FIG. 12 have been removed from the injection molding machine it is inserted manually into the guide formed by the profile 26 then to be advanced by the drive means along the process line. In order that the surface of the shanks shall be made optimally adherent the shanks are pretreated at 10–20 kV and 2–3 A then to be coated with glue, preferably a water-based setting glue, over a predetermined length at the brush end of the shank, i.e. over the end portion of the shank which is to be provided with fibers. This can be made according to FIG. 14. The lane formed by the profile 26 has a downward bow 29 so that the shanks 15 are lowered and also are mutually dispersed, and below said downward bow there is a trough with glue. In the glue trough a predetermined level is maintained by supplying glue from a supply vessel 31 and returning glue to said vessel via an overflow 32. Thus, an accurately defined end portion of the shank will be provided with glue when the shank during the movement thereof along the process line is immersed into the glue trough. The glue can be replaced by a solvent for the shank material so that the fibers are attached in a dissolved sticky surface layer of the shank, equivalent to a glue.

Figure 15:
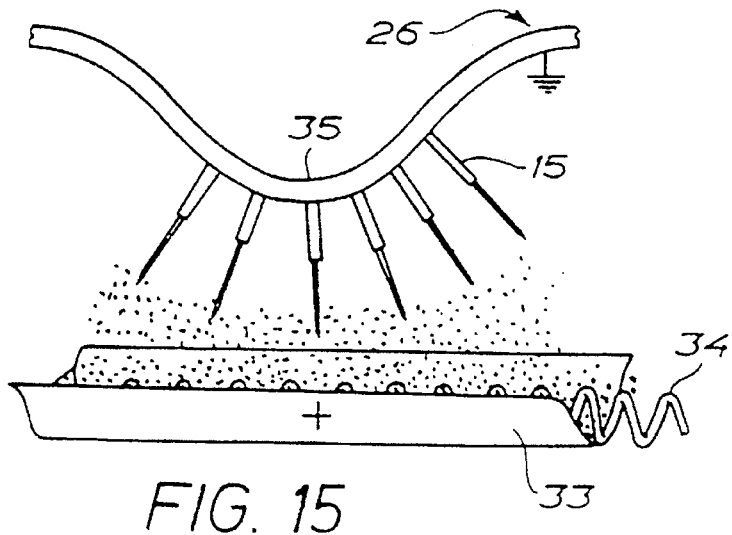
FIG. 15 is a diagrammatic side view of an apparatus for applying fibers to the glue coated shank ends by electrostatic flocculation.
Figure 16:
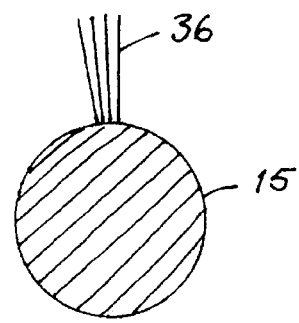
FIG. 16 is an enlarged cross-sectional view of the part of the shank carrying the fibers, showing some of the fibers attached to said surface.

In a following station shown in FIG. 15 application of fibers on the end portion of the shank provided with glue, then is effected by electrostatic flocculation. Fibers such as nylon fibers of a predetermined uniform length are received in a trough 33 connected to the positive pole of an AC source the voltage of which is e.g. 90 kV, and the fibers are supplied to the trough and are kept loose therein by means of a feeder screw 34. Also over the trough 33 the profile 26 forms a downward bow 35 so that the shanks will be moved downwards towards the trough and at the same time will be dispersed when they pass along the process line. The profile is grounded, i.e. it is connected to the negative pole of the high voltage source, and by known technique the fibers are drawn to the shanks where they are "shot" into the portion coated with glue and will be attached to said portion. As a consequence thereof they will form a velour finish over that part of the shank which is coated with glue, and in this part the fibers stand on end projecting from the shank perpendicularly to the tangent of the curved surface of the shank 15 as shown in FIG. 16 where only a few fibers 36 are shown. As will be understood the fibers are uniformly distributed on the curved surface over the total circumference of the shank. Between adjacent fibers there are formed spaces which widen from the ends of the fibers which are attached to the surface of the shank, towards the free ends of the fibers, and these spaces are ideal for retaining the material to be collected and also for giving off the material at the site where the material is to be deposited. The free ends of the fibers accurately reproduce the shape of the surface to which the fibers are attached, no cutting of the attached fibers being necessary. The density of the velour finish portion which thus forms the brush proper will be dependent on the dwelling time of the shank in the electrostatic field and of the strength thereof. After velour finishing the brushes are cut from the ingot and are enclosed in sterile packages.

A preferred diameter of the fibers is about 0.06 mm. In an embodiment for sampling in urethra the fibers had a diameter of 0.063 mm. The length of the fibers ranges from about 0.5 to about 1.5 mm. The preferred range is about 1 to about 1.5 mm. It is preferred to each the surface of the fibers to make the surface hydrofil in order to improve the collection and retaining of material between the fibers as well as the attachement of the fibers to the shank by gluing.

Nylon is the preferred material for the fibers but fibers of other material, preferably plastics, can be used in the brush of the invention.

We claim:

1. A method for medical sampling, comprising:

providing a collection instrument comprising
an elongated shank;
a body forming an axial extension of said elongated shank at a first end thereof, a second end of the elongated shank forming a handle where the brush is to be gripped manually for use, said body being substantially circular in a transverse cross section and forming a smooth surface extending continuously over the axial length of said body; and
a velour finish covering the smooth surface of the body over an entire circumference of the body, the velour finish including a plurality of fibers of a uniform length, each of the fibers having first and second ends, the fibers being glued to said surface at said first ends uniformly distributed over the surface, and the fibers projecting radially from the surface with said second ends defining a curved surface of the velour finish;
collecting biomaterial from a cervix onto the plurality of fibers;and
transferring the biomaterial onto a deposit site.

2. The method in accordance with claim 1, wherein the body is shaped to conform to the collection site.

3. The method in accordance with claim 1, wherein the body comprises a separate body connected to the shank.

4. The method in accordance with claim 1, wherein the body tapers from the shank toward the a end of the body.

5. The method in accordance with claim 1, wherein at least two flaps are provided at a base of said body projecting laterally from the shank.

6. The method in accordance with claim 1, wherein said body forms a circular disk, the shank being connected centrally and axially to the disk.

7. The method in accordance with claim 1, wherein the velour finish surface forms several axially spaced annular portions.

8. The method in accordance with claim 1, wherein the velour finish surface forms a helical string.

9. The method in accordance with claim 1, wherein the velour finish surface forms several radially spaced axial portions.

10. The method in accordance with claim 1, wherein the fibers have a diameter of about 0.06 mm.

11. The method in accordance with claim 1, wherein the fibers have uniform length.

12. The method in accordance with claim 11, wherein the length of the fibers ranges from about 0.5 to about 1.5 mm.

13. The brush in accordance with claim 11, wherein the length of the fibers ranges from about 1 mm to about 1.5 mm.

14. The method in accordance with claim 1, wherein the fibers have a length of at least 0.5 mm.

* * * * *

UNITED STATES PATENT AND TRADEMARK OFFICE
CERTIFICATE OF CORRECTION

PATENT NO. : 5,623,941

DATED : April 29, 1997

INVENTOR(S) : Hedberg et al.

It is certified that error appears in the above-identified patent and that said Letters Patent is hereby corrected as shown below:

First Page, in [63], line 2: "674,127, Oct. 3" should read --634,127, Jan. 3--

First Page, in [57], line 2: "wish" should read --with--

Col. 1, line 4: "1995" should read --1993--

Col. 1, line 5: "contruction" should read --continuation--

Col. 1, line 44: ", if" should read --. If--

Col. 2, line 45: "end" should read --and--

Col. 2, line 52: "FIG. 3" should not begin a new paragraph

Col. 2, line 54: insert --the-- after "having"

Col. 3, line 44: "pot%ion" should read --portion--

Col. 3, line 61: insert --at-- after "impressions"

UNITED STATES PATENT AND TRADEMARK OFFICE
CERTIFICATE OF CORRECTION

PATENT NO. : 5,623,941

DATED : April 29, 1997

INVENTOR(S) : Hedberg et al.

It is certified that error appears in the above-identified patent and that said Letters Patent is hereby corrected as shown below:

Col. 5, line 7: "underout" should read --undercut--

Col. 5, line 23: "lane" should read --line--

Col. 6, line 10: "material" should read --materials--

Signed and Sealed this

Twentieth Day of January, 1998

Attest:

BRUCE LEHMAN

Attesting Officer

Commissioner of Patents and Trademarks